US012698526B2

(12) United States Patent
Tanaka et al.

(10) Patent No.: US 12,698,526 B2
(45) Date of Patent: Aug. 4, 2026

(54) DNA DETECTION METHOD AND DEVICE THEREFOR

(71) Applicant: Hitachi, Ltd., Tokyo (JP)

(72) Inventors: Junko Tanaka, Tokyo (JP); Yoshinobu Kohara, Tokyo (JP); Kunio Harada, Tokyo (JP); Yu Ishige, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 15/755,957

(22) PCT Filed: Jul. 5, 2016

(86) PCT No.: PCT/JP2016/069887
§ 371 (c)(1),
(2) Date: Feb. 27, 2018

(87) PCT Pub. No.: WO2018/008083
PCT Pub. Date: Jan. 11, 2018

(65) Prior Publication Data
US 2018/0298435 A1    Oct. 18, 2018

(51) Int. Cl.
| | |
|---|---|
| *C12P 19/34* | (2006.01) |
| *B01J 19/00* | (2006.01) |
| *C12M 1/00* | (2006.01) |
| *C12Q 1/68* | (2018.01) |
| *C12Q 1/686* | (2018.01) |
| *C12Q 1/6869* | (2018.01) |
| *G16B 25/20* | (2019.01) |
| *G16B 99/00* | (2019.01) |
| *B01L 3/00* | (2006.01) |
| *B01L 7/00* | (2006.01) |

(52) U.S. Cl.
CPC ........ *C12Q 1/6869* (2013.01); *B01J 19/0046* (2013.01); *C12M 1/00* (2013.01); *C12Q 1/68* (2013.01); *C12Q 1/686* (2013.01); *G16B 25/20* (2019.02); *G16B 99/00* (2019.02); *B01L 3/502784* (2013.01); *B01L 7/52* (2013.01); *C12Q 2561/12* (2013.01); *C12Q 2563/107* (2013.01); *C12Q 2563/173* (2013.01)

(58) Field of Classification Search
CPC ............ C12Q 2563/159; C12Q 1/6806; C12Q 1/6844; C12Q 1/6851; C12Q 1/68; C12Q 1/6818; C12Q 1/6876; C12Q 2537/143; C12Q 1/6869; C12Q 2545/107; C12M 1/00
USPC ....... 435/6.1, 6.11, 6.12, 91.1, 91.2; 436/94, 436/501; 536/23.1, 24.3, 24.33, 25.3
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,800,159 | A | 1/1989 | Mullis et al. |
| 10,655,165 | B2 * | 5/2020 | Carlson ................. C12Q 1/6816 |
| 2006/0257893 | A1 * | 11/2006 | Takahashi .............. C12Q 1/686 435/6.12 |
| 2010/0092973 | A1 * | 4/2010 | Davies ............. B01L 3/502784 435/6.19 |
| 2011/0244455 | A1 | 10/2011 | Larson et al. |
| 2013/0178378 | A1 * | 7/2013 | Hatch ................... C12Q 1/686 506/9 |
| 2013/0190194 | A1 * | 7/2013 | Tang ...................... G16B 25/00 506/9 |
| 2014/0147851 | A1 | 5/2014 | Qian |
| 2014/0186827 | A1 * | 7/2014 | Pieprzyk .............. C12Q 1/6855 435/6.11 |
| 2014/0221238 | A1 * | 8/2014 | Regan .................. C12Q 1/6851 506/9 |

FOREIGN PATENT DOCUMENTS

| | | |
|---|---|---|
| JP | 2013-521764 A | 6/2013 |
| JP | 2014-510538 | 5/2014 |
| WO | WO 2011/100604 A2 | 8/2011 |

OTHER PUBLICATIONS

Lind et al "Combining sequence-specific probes and DNA binding dyes in real-time PCR for specific nucleic acid quantificaiton and melting curve analysis" BioTechniques, 2006, 40 (3): 315-318. (Year: 2006).*
"TaqMan" from Wikipedia. Printed on May 23, 2022.*
"Molecular beacon" from Wikipedia. Printed on Oct. 26, 2022.*
"Förster (Fluorescence) Resonance Energy Transfer with Fluorescent Proteins". Printed on Oct. 26, 2022.*
Rye et al., Interaction of dimeric intercalating dyes with single-stranded DNA. Nucleic Acids Research, 23, 1215-1222, 1995.*
"T7 DNA polymerase" from NEB. Printed on Sep. 30, 2023.*
"Molecular beacon" from Wikipedia. Printed on Jun. 29, 2024.*
Sekar et al., Fluorescence resonance energy transfer (FRET) microscopy imaging of live cell protein localizations. The Journal of Cell Biology, 160, 629-633, 2003.*
"Base pair" from Wikipedia. Printed on Sep. 4, 2025.*
C. Heid et al., "Real Time Quantitative PCR," Genome Research, Genome Methods, CSH Press, 1996, vol. 6., pp. 986-994, (Ten (10) pages).
International Search Report (PCT/ISA/210) issued in PCT Application No. PCT/JP 2016/069887 dated Oct. 11, 2016 with English translation (Four (4) pages).

(Continued)

*Primary Examiner* — Frank W Lu
(74) *Attorney, Agent, or Firm* — Crowell & Moring LLP

(57) ABSTRACT

The present invention was made to provide novel methods for detecting DNA and devices therefor. Specifically, the present invention is a method of detecting DNA including the steps of: adding, to an oil, a fluorescently-labeled probe, a DNA intercalator, and a DNA solution containing a target DNA to produce droplets; performing PCR on the droplets; and measuring fluorescence from the fluorescently-labeled probe and fluorescence from the DNA intercalator, wherein the DNA solution has a concentration at which each droplet is produced so as to contain one or less target DNA molecule. In addition, the present invention is a DNA detection device including a droplet production unit, a thermal cycler unit, and a fluorescence detection unit which perform these steps.

2 Claims, 5 Drawing Sheets

(56) References Cited

OTHER PUBLICATIONS

Japanese-language Written Opinion (PCT/ISA/237) issued in PCT Application No. PCT/JP2016/069887 dated Oct. 11, 2016 (Four (4) pages).

QX200 Droplet Digital PCR & AutoDG, "It starts with a Droplet and Ends in Discovery." Bio-Rad Laboratories, Inc. [Online], 2015.04, pp. 1-20, retrieval date Sep. 28, 2016, Internet: URL:http://www.bio-rad.com/webroot/web/pdf/is/japan/japanese/literature/C10581_QX200_ddPCR.pdf, particularly, pp. 4, 6 and 7, with partial translation.

G. McDermott et al., "Multiplexed Target Detection Using DNA-Binding Dye Chemistry in Droplet Digital PCR," Analytical Chemistry, ACS Publications, American Chemical Society 2013, vol. 85, pp. 11619-11627, particularly, abstract p. 11625, left column Fig. 6.

K. Lind et al., "Combining Sequence-Specific Probes and DNA Binding Dyes in Real-Time PCR for Specific Nucleic Acid Quantification and Melting Curve Analysis," Bio Techniques, 2006, vol. 40, No. 3, pp. 315-319, particularly, abstract, Fig. 1.

* cited by examiner

【FIG.1】
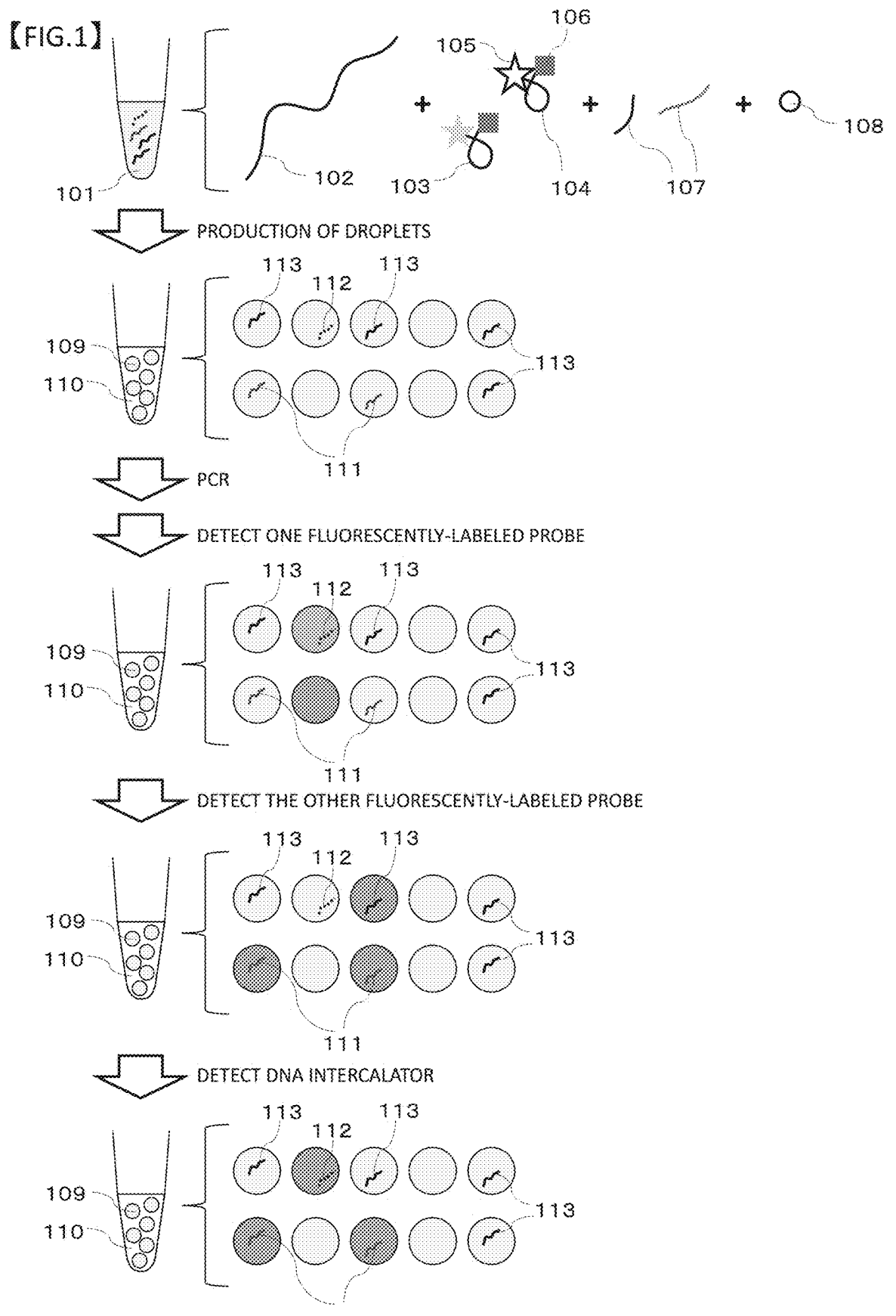

【FIG.5】

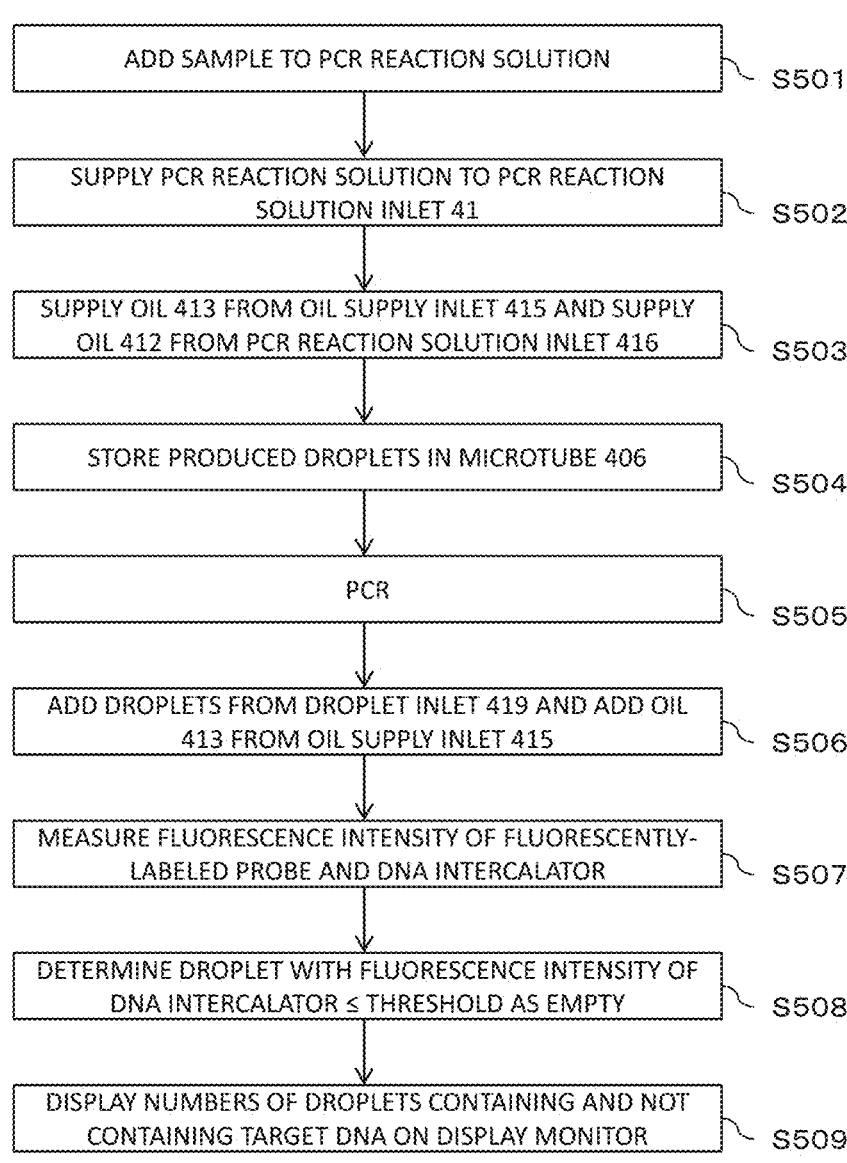

ADD SAMPLE TO PCR REACTION SOLUTION — S501

SUPPLY PCR REACTION SOLUTION TO PCR REACTION SOLUTION INLET 41 — S502

SUPPLY OIL 413 FROM OIL SUPPLY INLET 415 AND SUPPLY OIL 412 FROM PCR REACTION SOLUTION INLET 416 — S503

STORE PRODUCED DROPLETS IN MICROTUBE 406 — S504

PCR — S505

ADD DROPLETS FROM DROPLET INLET 419 AND ADD OIL 413 FROM OIL SUPPLY INLET 415 — S506

MEASURE FLUORESCENCE INTENSITY OF FLUORESCENTLY-LABELED PROBE AND DNA INTERCALATOR — S507

DETERMINE DROPLET WITH FLUORESCENCE INTENSITY OF DNA INTERCALATOR ≤ THRESHOLD AS EMPTY — S508

DISPLAY NUMBERS OF DROPLETS CONTAINING AND NOT CONTAINING TARGET DNA ON DISPLAY MONITOR — S509

DNA DETECTION METHOD AND DEVICE THEREFOR

BACKGROUND ART

In the diagnosis of cancers and infectious diseases, it is desired to quantify cancer-related genes and virus-derived genes which are present in a very small amount in samples, or to detect mutations that are present in a much smaller amount than the total amount of cancer-related genes of interest. So far, PCR (Patent Documents 1 to 3) and real-time PCR (Non-Patent literature 1) have been used for such genetic examinations. In recent years, however, desired is a method that enables reproducible as well as quantitative measurement in genetic examinations with a higher sensitivity than conventional methods because of extreme reduction of the sample amount or early diagnosis of a disease.

Droplet digital PCR (Patent Document 4) has been developed as a method of solving, by absolute quantification using limiting diluted samples, the problem that measurement reproducibility is lower when a target gene is present in a trace amount in conventional genetic examinations. An experimental procedure of droplet digital PCR is described below. First, in droplet digital PCR, samples are limiting diluted such that one or zero molecule of target genes is contained in a single droplet. Next, DNA polymerase, primers and a fluorescently-labeled probe necessary for PCR are added to the limiting diluted sample, and droplets of PCR reaction solution are produced in oil. After preparing the droplet, the target gene is amplified by PCR. The fluorescence intensity of each droplet is measured after the PCR, and the target gene is quantified by counting the number of droplets having a fluorescence intensity exceeding the threshold.

RELATED ART DOCUMENTS

Patent document 1: U.S. Pat. No. 4,683,195
Patent document 2: U.S. Pat. No. 4,683,202
Patent document 3: U.S. Pat. No. 4,800,159
Patent document 4: JP-T-2013-521764
Non-patent literature 1: Genome Res., 10, pp. 986-994, 1996

SUMMARY OF THE INVENTION

Problems to be Solved by the Invention

An object of the present invention is to provide novel methods of detecting DNA and devices therefor.

An aspect of the present invention is a method of detecting DNA including the steps of: adding, to an oil, a fluorescently-labeled probe, a DNA intercalator, and a DNA solution containing a target DNA to produce droplets; performing PCR on the droplets; and measuring fluorescence from the fluorescently-labeled probe and fluorescence from the DNA intercalator, wherein the DNA solution has a concentration at which each droplet is produced so as to contain one or less target DNA molecule. This DNA detection method may further include the step of determining, after measuring both fluorescences, a droplet for which at least one of the fluorescences is not detected as a droplet that does not contain the target DNA. The fluorescently-labeled probe may have a fluorescent dye and a quencher for the fluorescent dye. The fluorescence from the fluorescently-labeled probe and the fluorescence from the DNA interca-lator may be detected simultaneously or the fluorescence from the fluorescently-labeled probe may be detected prior to the fluorescence from the DNA intercalator. A wavelength of the fluorescence from the fluorescently-labeled probe may be shorter than that of the fluorescence from the DNA intercalator. Furthermore, oil may contain a fluorine-based oil, a silicone-based oil, or a hydrocarbon-based oil.

Another aspect of the present invention is a DNA detection device for detecting DNA including a droplet production unit for adding, to an oil, a fluorescently-labeled probe, a DNA intercalator, and a DNA solution containing a target DNA to produce droplets; a thermal cycler unit for performing PCR on the droplets; and a fluorescence detection unit for measuring fluorescence from the fluorescently-labeled probe and fluorescence from the DNA intercalator, wherein the DNA solution has a concentration at which each droplet is produced so as to contain one or less target DNA molecule. This DNA detection device may include a display monitor on which the number of the droplets containing the target DNA and the number of the droplets containing no target DNA are displayed. The fluorescently-labeled probe may have a fluorescent dye and a quencher for the fluorescent dye. The fluorescence from the fluorescently-labeled probe and the fluorescence from the DNA intercalator may be detected simultaneously or the fluorescence from the fluorescently-labeled probe may be detected prior to the fluorescence from the DNA intercalator. A wavelength of the fluorescence from the fluorescently-labeled probe may be shorter than that of the fluorescence from the DNA interca-lator. Furthermore, oil may contain a fluorine-based oil a silicone-based oil, or a hydrocarbon-based oil.

A yet another aspect of the present invention is a program for making a DNA detection device perform any one of the aforementioned methods. This DNA detection device may any one of the aforementioned DNA detection devices.

BRIEF DESCRIPTION OF THE DRAWINGS

FIG. 1 is a diagrammatic representation showing steps of a method of detecting DNA according to an embodiment of the present invention.

FIG. 5 is a flowchart showing a method of detecting DNA using the device and the cartridge shown in FIG. 4 in an embodiment of the present invention.

EMBODIMENTS FOR CARRYING OUT THE INVENTION

Figures 2A, 2B:
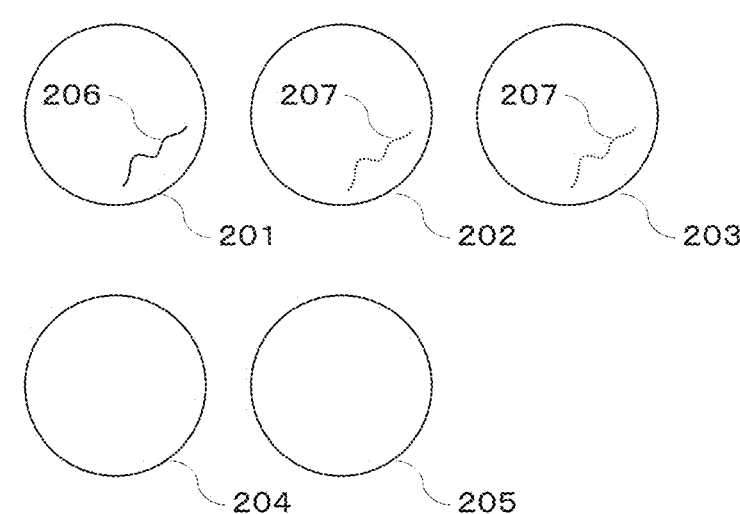
FIGS. 2A and 2B are diagrams showing a combination of droplets and their fluorescence in an embodiment of the present invention.

The objects, features, advantages, and ideas of the present invention will be apparent to those skilled in the art from the description of the present specification, and those skilled in the art can easily reproduce the present invention from the description of the present specification. Embodiments and specific examples of the invention described below indicate preferred embodiments of the present invention and are given for the purpose of illustration or explanation. They do not limit the present invention thereto. It will be apparent to those skilled in the art that various changes and modifications can be made based on the description herein within the spirit and scope of the present invention disclosed herein.

(1) Methods of Detecting DNA

A method of detecting DNA according to the present invention includes the steps of adding, to an oil, a fluorescently-labeled probe, a DNA intercalator, and a DNA solution containing a target DNA to produce droplets; performing PCR on the droplets; and measuring fluorescence from the fluorescently-labeled probe and fluorescence from the DNA intercalator. Hereinafter, the invention is specifically described with reference to an embodiment, but the present invention is not limited to this embodiment.

FIG. 1 shows steps of a method of detecting DNA in an embodiment of the present invention. First, DNA polymerase, primers 107, fluorescently-labeled probes 103, 104 each of which is labeled with a different fluorescent dye for recognizing a different sequence, DNA intercalator 108, deoxyribonucleotides, and a buffer solution are added to a sample containing target DNA 102 to prepare a PCR reaction solution 101.

The sample may be any material containing target DNA, and examples thereof include biological samples such as body fluids and tissues of animals and plants, cells, and excrements, and soil samples containing fungi or bacteria. Examples of the body fluids include blood, saliva, and cerebrospinal fluid. Examples of the tissues include a portion of an affected site obtained by surgery or biopsy (for example, cancer tissues of breast or liver). Examples of the cells include those present around an affected site collected by a biopsy method and tumor cells circulating in the blood. These samples may be a homogenate, a suspension or a solution of samples collected from a living body or an environment, but those obtained by the purification of nucleic acids therein are preferable.

Each of the fluorescently-labeled probes 103 and 104 has a fluorescent dye 105 and a quencher 106 for the fluorescent dye 105 at the 5' and 3' ends, respectively. The fluorescently-labeled probes 103 and 104 may be TaqMan® probes that anneal to a template DNA and then are hydrolyzed by the exonuclease activity of the Taq DNA polymerase so that the fluorescent dye and the quencher are separated with each other and fluorescence is emitted or Molecular Beacons that are generally in a stem-and-loop structure but anneal to a template DNA so that the fluorescent dye and the quencher are separated with each other and fluorescence is emitted. The fluorescently-labeled probes 103 and 104 may be at any concentration but the concentration is preferably about the same as that of the primers and between 0.01 µM and 1 µM.

Any combination of the fluorescent dye 105 and the quencher 106 usually used in real-time PCR can be used for the fluorescently-labeled probes 103 and 104. Examples of the fluorescent dye 105 include FAM, VIC, ROX, Cy3, and Cy5 and examples of the quencher 106 include TAMRA, BHQ1, BHQ2, and BHQ3.

The DNA sequences recognized by the fluorescently-labeled probes 103 and 104 may be completely different or may be different by one base. For example, in the case of genes, the sequences may be of different genes, or may be of a wild-type and a mutant of a gene. For example, in the case of genetic testing of lung cancer, the presence or absence of ALK fusion gene and EGFR gene mutation is determined in order to predict the efficacy of a molecular targeted drug. At that time, sequences may recognize each of the ALK fusion gene and the EGFR gene, or may recognize each of the L858R mutant and the wild-type of EGFR.

The DNA intercalator 108 can be used as long as they bind to double-stranded DNA in PCR, resulting in an increase in fluorescence intensity and can thus be used to detect DNA. Specific examples of the intercalator 108 that can be used include SYBR® Green I, SYBR Gold, PicoGreen®, SYTO® Blue, SYTO Green, SYTO Orange, SYTO Red, POPO®-1, BOBO®-1, YOYO®-1, TOTO®-1, JOJO®-1, POPO-3, LOLO®-1, BOBO-3, YOYO-3, TOTO-3, PO-Pro®-1, YO-Pro®-1, TO-Pro®-1. JO-Pro®-1, PO-Pro-3, YO-Pro-3, TO-Pro-3, TO-Pro-5, and ethidium bromide. When a DNA intercalator are used for DNA detection, an excessive amount is typically added to increase the fluorescence intensity and improve the accuracy. In contrast, the present invention only requires the DNA intercalator to enable determination of the presence or absence of amplification of certain DNA and does not require any quantitative results. Accordingly, the concentration of the DNA intercalator may be about the same as or even lower than that of the primers 107. Specifically, the concentration is preferably between 0.001 µM and 1 µM. Furthermore, the DNA intercalator may be added to not only the PCR reaction solution but also the oil used for preparing the droplets.

Next, droplets 109 are produced using the PCR reaction solution 101 and a mixed solution 110 of the oil and a surfactant. At this time, the dilution ratio of the sample is adjusted so as to include one or zero target DNA molecule 111, 112 in each droplet. The droplet may have any size but it is preferable that the size is between 10 µm and 100 µm. For example, assuming that the size of each droplet is 20 µm on average, the average volume per droplet is 4 pl. If it is intended that each droplet of 4 pl contains one genome of 3.2 pg, the sample should be diluted to the final concentration of 800 ng/µl. This concentration, however, is practically more likely to result in droplets each containing two or more genomes. For this reason, the final concentration of DNA is preferably 80 ng/µl or lower, which is one tenth of the aforementioned value. The lower limit is preferably at 0.8 ng/µl or higher, which is $\frac{1}{1,000}$ and more preferably at about 8 ng/µl which is $\frac{1}{100}$.

Droplets may be produced using any known method. Examples include a method of producing droplets by mixing oil, a surfactant, and a PCR reaction solution in a microchannel, a method of producing droplets by adding a PCR reaction solution to a layer of oil and surfactant through a porous membrane, and a method of producing droplets by mixing and stirring, with a vortex mixer, oil, a surfactant, and a PCR reaction solution in a tube.

Oil is a chemically inert substance which is insoluble or hardly soluble in the PCR reaction solution constituting the droplets, and is preferably a substance which is stable against change in temperature at high temperature such as PCR. Fluorine-based oils, silicone-based oils, and hydrocarbon-based oils can be used. Examples of the fluorine-based oils include perfluorocarbon and hydrofluoroether. Fluorine-based oils having longer carbon chains are preferable because of their lower volatility. In addition, since fluorine-based oils have a specific gravity of greater than 1.7 and are denser than water with a specific gravity of 1 which serves as the solvent of the PCR reaction solution, the droplets produced float on the oil. Examples of the silicone-based oils include polyphenylmethylsiloxane and trimethvlsiloxysilicate. Unlike the fluorine-based oils, silicone-based oils have a specific gravity of about 0.98 which is closer to that of water as a solvent of the PCR reaction solution. Accordingly, the droplets produced are uniformly distributed in oil Examples of the hydrocarbon-based oils include mineral oils, liquid paraffin, and hexadecane. Since the hydrocarbon-based oils have a specific gravity of about 0.84 and are less dense than water which serves as the solvent of the PCR reaction liquid, the droplets produced sink in the oil.

The surfactant may be of any kind, but Tween 20, Tween 80, Span 80. Triton X-100 can be used.

PCR is performed on the droplets produced with a thermal cycler to amplify the target DNA in the droplets. After completion of the reaction, the fluorescence intensity of each droplet is measured.

FIG. 2 shows an example of combinations of expected droplets and their fluorescence. For five kinds of droplets 201 to 205, FIG. 2A shows the state of droplets before PCR, and FIG. 2B shows the states of droplets after PCR. In the states before PCR shown in FIG. 2A, only the DNA contained in the droplets are illustrated, and the fluorescently-labeled probe and the DNA intercalator are not shown. The droplet 201 contains the target DNA 206, the droplets 202 and 203 contains a DNA 207 which is not the detection target, and the droplets 204 and 205 do not contain DNA. As shown in FIG. 2B, since the droplets 202 and 204 do not contain the target DNA 206, a fluorescently-labeled probe 208 is not degraded and a DNA intercalator 209 is not intercalated; accordingly, no fluorescence is detected. Since the droplet 201 contains the target DNA 206, the fluorescently-labeled probe is degraded and a fluorescent dye 210 and a quencher 211 become separated as the amount of amplified DNA increases. Furthermore, a DNA intercalator 212 intercalates with the amplified DNA and fluorescences of the fluorescently-labeled probe and the DNA intercalator are detected. The droplets 203 and 205 show the cases where the target DNA 206 is not contained but the fluorescently-labeled probe is degraded or the fluorescent dye 210 and the quencher 211 of the fluorescent probe are separated due to a component derived from the sample and thus fluorescence is emitted from the fluorescent dye 210 of the fluorescently-labeled probe. In contrast, since the DNAs are not amplified in the droplets 203 and 205, the DNA intercalator 209 does not emit fluorescence. Therefore, the number of the target DNA molecules 206 can be determined by counting the number of droplets in which the fluorescences of both the fluorescently-labeled probe and the DNA intercalator are detected, and the number of droplets that do not contain the target DNA 206 can be determined by counting the number of droplets in which one or either of the fluorescence is not detected. As can be seen from the above, according to the present invention, the amplified DNA is detected using two methods based on different mechanisms, and therefore, it is possible to significantly reduce possibility of producing pseudo-positives and improve the reproducibility and accuracy of measurement.

When two or more different kinds of target DNA 206 are present, it is possible, by using fluorescently-labeled probes labeled with different fluorescent dyes for different types of DNA, to determine the identity of DNA contained in each droplet according to the type of the fluorescent dye of the fluorescently-labeled probe.

Figure 3A:
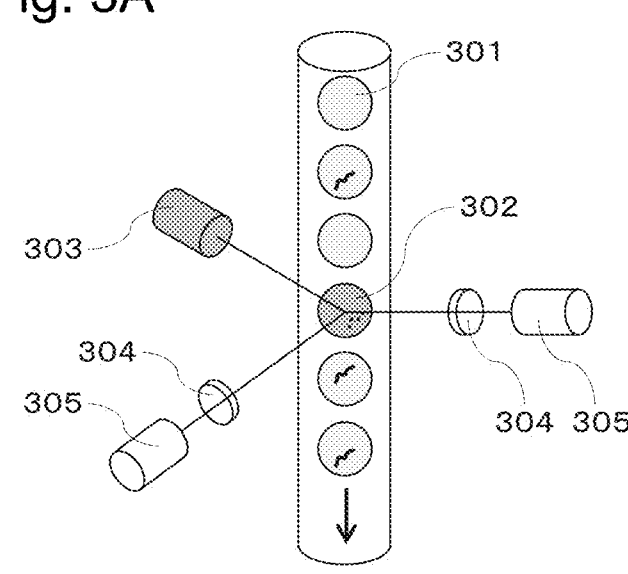
FIGS. 3A and 3B are diagrams showing a method of measuring a fluorescence intensity of each droplet in an embodiment of the present invention.

FIG. 3 shows an example of a method of measuring the fluorescence intensities of droplets. FIG. 3A shows a method of measuring the fluorescence intensities of droplets using a microchannel. Droplets 301 flow through the microchannel in the direction depicted by an arrow. When a droplet flows to a position where a droplet 302 is illustrated, it is exposed to the excitation light from a laser 303. A fluorescent substance contained in the droplet is excited by the laser 303, and fluorescence emitted is detected by a photomultiplier 305 through a fluorescence filter 304. A fluorescence detector composed of the laser 303, the fluorescence filter 304, and the photomultiplier 305 may be provided separately for detecting the fluorescently-labeled probe and the DNA intercalator; or as shown in FIG. 3, a fluorescence detector may be configured such that fluorescent substances are excited using the excitation light from a single laser and fluorescences are detected simultaneously using three band-pass filters.

Figure 3B:
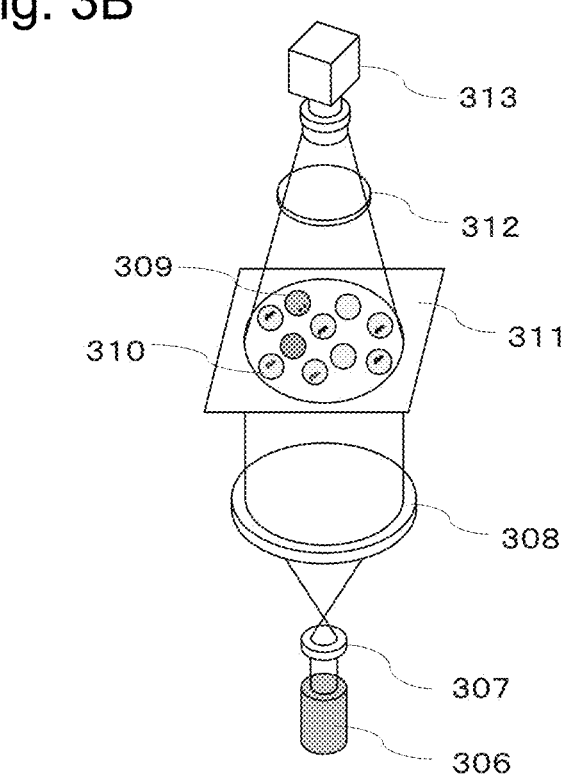

FIG. 3B is a diagram showing a method of placing droplets on a flat surface and measuring their fluorescence intensities. A solution containing droplets is placed on a stage 311. When the oil is hydrocarbon-based oil, the droplets sink in the solution and do not move on the stage 311; thus, the positions of the droplets can be determined and the number of the droplets can be counted. However, droplets float on the solution with fluorine-based oil, while they are distributed in the solution with silicone-based oil; accordingly, to detect fluorescence with the droplets fixed on the stage, a process is needed such as placing a solution containing droplets in a space between glass plates at an interval equal to or smaller than the diameter of the droplets. The droplets are exposed with the excitation light through lenses 307 and 308 by a laser 306 after placing the droplets in a manner as described above; then, the fluorescent substances contained in the droplets is excited and fluorescence is emitted The fluorescence emitted from the fluorescent substances is captured using a CCD camera 313 after removing the wavelengths of the excitation light by a fluorescence filter 312. The fluorescence filter 312 may be a long-pass filter that removes the wavelengths of the excitation light, or it may be band-pass filters each passes different wavelengths for the fluorescently-labeled probe and the DNA intercalator.

A desired combination of the wavelengths of the fluorescent dye and the DNA intercalator of the fluorescently-labeled probe depend on the order of detection. The DNA intercalator needs only to enable determination of the presence or absence of DNA amplification and therefore, their intensities are not required to be quantitative. In contrast, since the intensity of the fluorescent dye of the fluorescently-labeled probe should be measured accurately, preferable are conditions under which the fluorescent dye of the fluorescently-labeled probe is not affected such that the color is faded as a result of the measurement of the DNA intercalator. Therefore, when the fluorescence of the fluorescently-labeled probe is measured prior to that of the DNA intercalator or when the fluorescently-labeled probe and the DNA intercalator are excited by the excitation light emitted from a single laser to detect their fluorescence simultaneously using two band-pass filters, then the wavelengths of the fluorescent dye of the DNA intercalator are not so critical. However, when the fluorescence of the DNA intercalator is measured before that of the fluorescently-labeled probe, it is preferable to choose a fluorescent dye with a shorter wavelength for the fluorescently-labeled probe than for the DNA intercalator because this reduces the possibility that the fluorescent dye of the fluorescently-labeled probe lose its color due to the measurement of the DNA intercalator.

(2) DNA Detection Device

A DNA detection device according to an embodiment of the present invention includes a droplet production unit for producing droplets by adding, to oil, a fluorescently-labeled probe, a DNA intercalator, and a DNA solution containing a target DNA; a thermal cycler unit for performing PCR on the droplets, and a fluorescence detection unit for measuring fluorescence emitted by the fluorescently-labeled probe and the DNA intercalator. The invention is described specifically below with reference to an example but the present invention is not limited to the example.

Figure 4A:
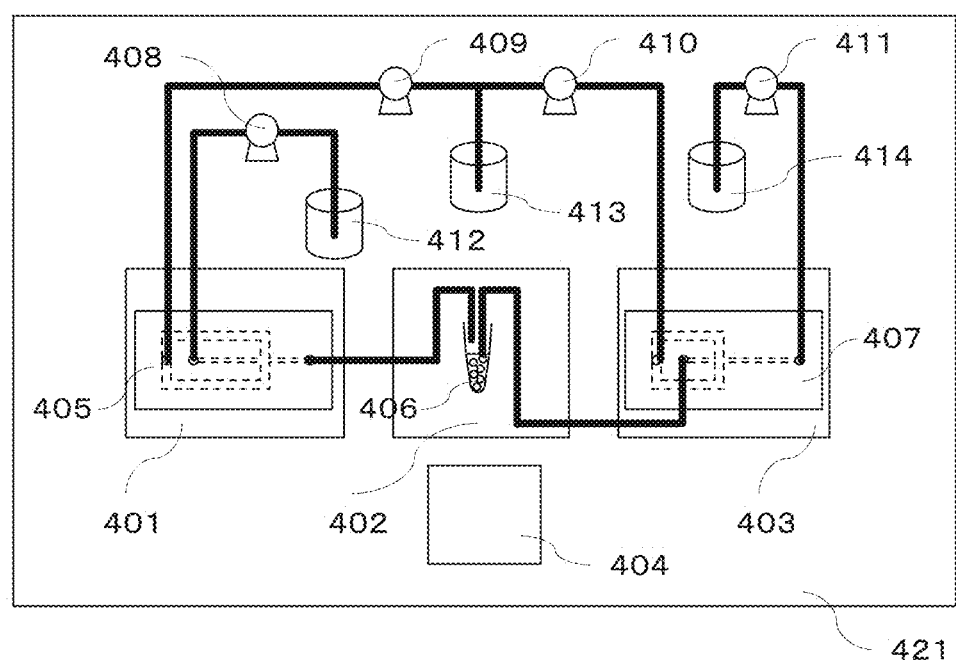
FIGS. 4A to 4C are diagrammatic representations showing a device with which a method of detecting DNA is performed and a cartridge used in the device according to an embodiment of the present invention.
Figure 4B:
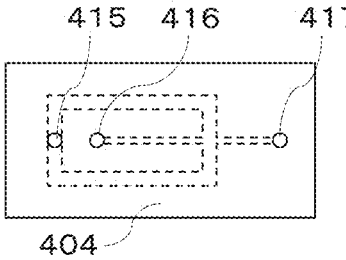
Figure 4C:
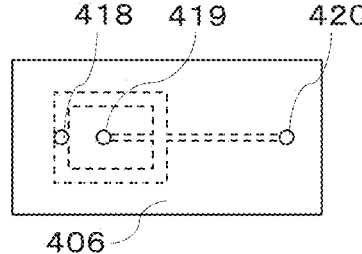

FIG. 4 is a diagram showing an example of a device for implementing the method of the present invention and a cartridge used in this device. As shown in FIG. 4A, a droplet digital PCR measurement apparatus 421 is composed of a droplet production unit 401, a thermal cycler 402, a droplet detection unit 403, and a display monitor 404. The droplet production unit 401 is used with a droplet production cartridge 405 shown in FIG. 4B loaded thereon. The droplet production cartridge 405 has an oil supply inlet 415, a PCR reaction solution inlet 416, and a droplet discharge outlet 417. The droplet detection unit 403 is used with a droplet detection cartridge 407 loaded thereon. The droplet detection cartridge 407 has an oil supply inlet 418, a droplet inlet 419, and a waste liquid discharge outlet 420. The oil supply inlet 415 of the droplet production cartridge 405 is in fluid communication with the droplet digital PCR measurement apparatus 421 and is supplied with oil 413 by a pump 409. The PCR reaction solution inlet 416 of the droplet production cartridge 405 is in fluid communication with the droplet digital PCR measurement apparatus 421 and is supplied with gas such as nitrogen gas or air or with oil 412 by a pump 408. The droplet discharge outlet 417 of the droplet production cartridge 405 is in fluid communication with the droplet digital PCR measurement apparatus 421 and is connected to a microtube 406 mounted in the thermal cycler 402. The oil supply inlet 418 of the droplet detection cartridge 407 is in fluid communication with the droplet digital PCR measurement apparatus 421 and is supplied with the oil 413 by a pump 410. The droplet inlet 419 of the droplet detection cartridge 407 is in fluid communication with the droplet digital PCR measurement apparatus 421 and is connected to the microtube 406 mounted in the thermal cycler 402. The waste liquid discharge outlet 420 of the droplet detection cartridge 407 is in fluid communication with the droplet digital PCR measurement apparatus 421 and the waste liquid in the droplet detection cartridge 407 is discharged into a waste liquid reservoir 414 by a pump 411. Each of the pumps may be a peristaltic pump, a syringe pump, or a diaphragm pump. The display monitor 404 serves as a display unit on which results of measurement and messages are displayed and an input unit with which a user enters his or her commands.

FIG. 5 is a diagram illustrating an example of a measurement method using the device and the cartridges shown in FIG. 4. The sample used here is purified DNA collected from a biological material and the sample is added to a PCR reaction solution containing DNA polymerase, primers, a fluorescently-labeled probe, a DNA intercalator, deoxyribonucleotides, and buffer (S501). In this case, for the fluorescently-labeled probe, used is a TaqMan probe that is hydrolyzed by DNA polymerase and emit fluorescence. The PCR reaction solution in the droplet production cartridge 405 is supplied to the PCR reaction solution inlet 416 (S502). The droplet production cartridge 405 is mounted to the droplet production unit 401 of the droplet digital PCR measurement apparatus 421. The oils 413 and 412 are supplied from the oil supply inlet 415 and the PCR reaction solution inlet 416, respectively (S503). Droplets are produced at an intersection where the oil in the droplet production cartridge 405 crosses the flow passage of the PCR reaction solution. The produced droplets are discharged through the droplet discharge outlet 417 and are stored in the microtube 406 which has been installed in the thermal cycler in advance (S504). The lid of the microtube 406 is closed, and the PCR reaction is performed under the temperature control by the thermal cycler (S505). As the reaction cycles proceed, the DNA sequence is amplified and the fluorescently-labeled probe are degraded, resulting in an increase in fluorescence intensity. Synthesized DNA forms a double-strand with which the DNA intercalator intercalates to emit fluorescence. After the completion of the reaction, droplets and the oil 413 are added from the droplet inlet 419 and the oil supply inlet 415, respectively, of the droplet detection cartridge which has been loaded on the droplet detection unit 403 in advance (S506). In the droplet detection unit, the fluorescence intensities of the fluorescently-labeled probe and the DNA intercalator are measured (S507). A droplet with a fluorescence intensity of the DNA intercalator being equal to or lower than a threshold is determined to be empty (S508). The threshold may be, for example, one tenth of the maximum fluorescence intensity expected to the DNA intercalator but is not limited thereto. The droplets yielding high fluorescence intensities for both of the fluorescently-labeled probe and the DNA intercalator are determined to contain the target DNA, those in which one or either of the fluorescence are not detected are determined to be empty, and then the number of the droplets containing the target DNA and the number of the droplets that do not contain the target DNA are displayed on the display monitor (S509).

(3) Program

An embodiment of the present invention is a program for making a DNA detection device perform a method of detecting DNA. The DNA detection device used here is the device described in detail in the section (2) and the method described in detail in the section (1) is performed as the DNA detection method.

INDUSTRIAL APPLICABILITY

The present invention made it possible to provide novel methods of detecting DNA and devices therefor.

DENOTATION OF SYMBOLS

101 PCR reaction solution
102 DNA
103, 104 fluorescently-labeled probe
105 fluorescent dye
106 quencher
107 primer
108 DNA intercalator
109 droplet
110 mixed solution of oil and surfactant
111 target DNA molecule (A)
112 target DNA molecule (B)
113 non-target DNA molecule
201-205 droplets
206 target DNA molecule
207 non-target DNA molecule
208 fluorescently-labeled probe
209 DNA intercalator
210 fluorescent dye
211 quencher
212 DNA intercalator
301, 312 droplets
303 laser
304 fluorescence filter
305 photomultiplier
306 laser
307, 308 lenses
309 droplet
310 droplet 311 stage
312 fluorescence filter
313 photomultiplier
401 droplet production unit
402 thermal cycler
403 droplet detection unit
404 display monitor
405 droplet production cartridge
406 microtube
407 droplet detection cartridge
408-411 valves
412 oil
413 oil
414 waste liquid reservoir
415 oil supply inlet
416 PCR reaction solution inlet
417 droplet discharge outlet
418 oil supply inlet
419 droplet inlet
420 waste liquid discharge outlet
421 droplet digital PCR measurement apparatus

The invention claimed is:

1. A method of determining whether a solution contains a target DNA molecule, the method comprising the steps of:

produce droplets by adding a fluorescently-labeled probe, a DNA intercalator that binds to a double stranded DNA but not to an oil single stranded DNA, and the solution to an oil, each of the droplets containing the fluorescently-labeled probe, the DNA intercalator and the solution, the fluorescently-labeled probe having a fluorescent dye capable of producing a first fluorescence and a quencher of the fluorescent dye located at its 5' and 3' ends respectively, wherein the DNA intercalator emits a second fluorescence only when it intercalates into a double-strand DNA, and wherein each of the droplets has only one or zero of the target DNA molecule when the solution contains the target DNA molecule, and the fluorecently-labeled probe does not emit the first fluorescence before it interacts with the target DNA molecule;

performing a polymerase chain reaction (PCR) in the droplets using a DNA polymerase; and only after completion of the PCR, measuring the first fluorescence from the fluorescently-labeled probe and the second fluorescence from the DNA intercalator in the droplets by a fluorescence detector, wherein measuring the first fluorescence in the droplets using a fluorescence detector, the solution contains the target DNA molecule, when both the first fluorescence and the second fluorescence are detected in the droplets;

the solution does not contain the target DNA molecule, when the second fluorescence is not detected in the droplets;

wherein the wavelength of the first fluorescence and the wavelength of the second fluorescence are different; and wherein the DNA polymerase is a Taq DNA polymerase having 5' to 3' exonuclease activity and the fluorescently-labeled probe is a single-stranded hydrolysis probe that anneals to the target DNA molecule and then is hydrolyzed by exonuclease activity of the Taq DNA polymerase during the process of the PCR when the target DNA molecule is present in the droplet such that the fluorescent dye and the quencher located at 5' and 3' ends of the fluorexcently-labeled probe respectively are separated from each other and the first fluorescence is emitted in the droplets.

2. The method according to claim 1, wherein the oil comprises a fluorine-based oil, a silicone-based oil, or a hydrocarbon-based oil.

* * * * *